(12) United States Patent
Sprengers et al.

(10) Patent No.: US 8,765,058 B2
(45) Date of Patent: Jul. 1, 2014

(54) EXCHANGEABLE CONSUMABLE WITH INTEGRATED AIR FILTER

(75) Inventors: Wolfgang Sprengers, Hl. Kreuz am Waasen (AT); Berndt Ebner, Graz (AT); Andreas Riegelnegg, Graz-Weinitzen (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 830 days.

(21) Appl. No.: 12/269,385

(22) Filed: Nov. 12, 2008

(65) Prior Publication Data

US 2009/0169429 A1 Jul. 2, 2009

Related U.S. Application Data

(60) Provisional application No. 60/987,450, filed on Nov. 13, 2007.

(51) Int. Cl.
| | | |
|---|---|---|
| G01N 15/06 | (2006.01) | |
| A61B 5/145 | (2006.01) | |
| A61B 5/1468 | (2006.01) | |

(52) U.S. Cl.
CPC ............ *A61B 5/1468* (2013.01); *A61B 5/14546* (2013.01); *A61B 2560/0443* (2013.01)
USPC .................... 422/68.1; 422/82.01; 422/82.02; 422/82.03; 422/82.04; 422/82.05; 422/82.06; 422/82.07; 422/82.08; 422/82.09; 422/82.11; 422/82.12; 422/82.13; 422/500; 422/501; 422/513; 422/534; 422/547; 422/554; 422/939; 422/946; 422/948; 436/174; 436/177; 435/295.1; 435/295.3; 435/297.1

(58) Field of Classification Search
USPC .......... 422/68.1, 82.01–82.13, 500, 501, 513, 422/534, 547, 554, 939, 946, 948; 436/174, 436/177; 435/295.1, 295.3, 297.1
See application file for complete search history.

(56) References Cited

U.S. PATENT DOCUMENTS

| | | | |
|---|---|---|---|
| 2004/0189311 A1 | 9/2004 | Glezer et al. | |
| 2006/0013726 A1 | 1/2006 | Munenaka | |
| 2007/0253463 A1* | 11/2007 | Perry et al. | ..................... 374/208 |
| 2009/0142745 A1* | 6/2009 | Breidenthal et al. | .............. 435/3 |

FOREIGN PATENT DOCUMENTS

WO        2006132666 A1    12/2006

* cited by examiner

*Primary Examiner* — Dennis M White
(74) *Attorney, Agent, or Firm* — Roche Diagnostics Operations, Inc.

(57) ABSTRACT

The invention concerns an analyzer, typically for analyzing body fluids, which has one or several exchangeable cassettes (consumables) that contain operating liquids, operating materials and/or consumables and can be inserted into corresponding holders of the analyzer, wherein the analyzer has a system for exchanging ambient air which has a filter unit on the inlet side of the analyzer to filter the ambient air that needs to be exchanged. The filter unit is integrated into at least one of the exchangeable cassettes in order to minimize the amount of maintenance for the analyzer.

18 Claims, 2 Drawing Sheets

EXCHANGEABLE CONSUMABLE WITH INTEGRATED AIR FILTER

BACKGROUND OF THE INVENTION

The invention concerns an analyzer, typically for analyzing body fluids, that has one or more exchangeable cassettes (consumables) which contain operating liquids, operating agents and/or consumables, and which can be inserted into appropriate holders of the analyzer wherein the analyzer comprises a system for the exchange of ambient air which has a filter unit on the inlet side of the analyzer. In addition the invention concerns cassettes which can be inserted into such an analyzer in an exchangeable manner and which contain operating fluids, operating materials and/or consumables for the operation of the analyzer.

Exchangeable consumables refers to exchangeable consumables or containers or packs which contain consumables which can be exchanged regularly (for example, when a certain period has elapsed, or when a certain number of measurements has been carried out, or when a certain amount of operating material has been consumed) and can be inserted by operating personnel into an analyzer and, in particular, into an analyzer for analyzing body fluids.

Such analyzers for analyzing body fluids are, for example, developed as portable analyzers for determining POC (point of care) parameters, i.e., the blood gases ($O_2$, $CO_2$, pH), the electrolytes (e.g., $K^+$, $Na^+$, $Ca^{++}$, $Cl^-$), the metabolites (e.g., glucose and lactate), the haematocrit, the haemoglobin parameters (e.g., tHb, $SO_2$, etc.) and bilirubin, and are primarily used for the decentralized determination of the above-mentioned parameters in whole blood samples. Applications in veterinary medicine and the use of serum, plasma, urine and dialysate samples are possible.

Ideally it should also be possible for "untrained" users to simply and intuitively operate such analyzers. Another advantageous feature is when the instrument can be operated "virtually maintenance free" from the point of view of a user. "Virtually maintenance free" is generally understood as a system that requires as little maintenance as possible in which even a (technically) untrained user can only exchange consumables that are present in the form of cassettes and/or modules for the routine operation similar to for example an inkjet printer. It should be possible for the user to exchange all consumables by simple intuitive handling steps.

In one possible concept of such an analyzer, materials that are consumed can for example be combined as follows into consumables:

Consumable 1: Sensor cassette which contains all or at least some of the sensors required for the analyte determination.

Consumable 2: Liquid container or fluid pack which contains the functional fluids required to operate the analyzer (e.g., calibration solutions, washing solutions, reference liquids, certain reagent solutions required for the operation, etc.). It can optionally also contain further elements or functionalities such as the entire fluidic system or parts thereof, the sample input device or also further sensory components.

Consumable 3: Printer paper for an internal printer.

Consumable 4: Optionally further consumables may be provided, for example a cassette with reference solutions in ampoules for carrying out an automated quality control (aQC), which the user himself should be able to exchange by simple intuitive handling steps.

The subdivision of the consumables described above is only intended as an example of an embodiment variant. It is also conceivable that (partial) functionalities or (partial) elements of several consumables are combined so that for example fewer consumables or even only one consumable is required. On the other hand, it is also conceivable that (partial) functionalities or (partial) elements of individual consumables are distributed among several consumables.

The consumables are connected to one another and to the analyzer by matching interfaces e.g., in the form of fluidic docking nipples. The consumables can be mechanically connected to their respective counterparts by a simple manual sequence of movements either directly by the user or by drives located in the device which automatically carry out the coupling after the user has only brought the cassette into "position." or into a corresponding holder.

Medical analyzers have many electronic components which require an ambient temperature which is as constant as possible for a reliable operation.

Furthermore, the temperature of the sensory areas of the analyzer often also have to be kept constant within certain temperature ranges in order to provide the sensors with an operating environment that is as ideal as possible. Thus, for example enzyme sensors for glucose or lactate determination have to be maintained at a temperature of 30° C. for reasons of storage stability whereas for example sensors for blood gas determination can also be preferably operated at 37° C.

The functional fluids that are for example contained in the fluid pack also have certain preferred temperature conditions. Thus, for example certain solutions can be made stable for longer periods by storing them at lower temperatures.

Furthermore, medical analyzers are used worldwide under very different climatic boundary conditions which is why they have to reliably operate in a large range of temperatures and/or air humidities.

In summary it is apparent that medical analyzers have to have a reliable good temperature management and must have devices for this purpose which enable a controlled operating temperature that is as independent as possible of environmental conditions and the current operating status of the analyzer.

One component of the temperature management of such medical analyzers are ventilation systems which can dissipate waste heat in a directed manner by for example sucking in the surrounding air via special ventilation channels for cooling.

Since foreign bodies contained in the surrounding air (e.g., dust, particles, moisture droplets) are also sucked in and can thus reach the interior of the analyzer, such ventilation systems have air filters especially in their suction ducts which filter the sucked air in order to protect as far as possible the interior of the analyzer from such contaminations.

Separators are generally referred to as air filters which filter out undesired suspended matter such as microorganisms, pollen, dust or gases from the air. These are filtering separators which remove substances from an air flow in a filter medium. Usually fibres or particles are used as a filter medium (collectors). A distinction is for example made between fiber layer filters, granular bed filters and filters with a solid medium (more rarely such as sinter layers, ceramics).

As a result of the flow of surrounding air through the air filter, impurities accumulate on the inner surfaces of the air filter which reduces its filtering efficiency during the course of use.

In order to ensure that there is as far as possible always a good filtering efficiency and in particular a high rate of air flow while retaining all possible suspended matter, air filters have to therefore be exchanged at regular intervals.

Such exchange steps have previously had to be carried out in known instruments by the operator who manually had to remove the contaminated air filter from the instrument and had to replace it by a new air filter.

Since such exchange processes are not part of the daily routine operation of a medical analyzer they are not given priority in training and practice, so that they are therefore more subject to errors or generally omitted.

In addition the periods of use of such air filters in an instrument and also their degree of contamination is often not monitored so that the user would have no indication that an air filter replacement is due.

Air filters are configured as additional consumables in the analyzers known in the prior art which are inserted into the analyzer and which require a separate training in their handling and separate stock keeping. This can result in problems in handling (e.g., incorrect insertion) or also problems in their availability (lack of stock).

The result of such problems can for example be a defective analyzer due to contaminations that have entered or the analyzer may be temporarily blocked for further measurements due to incorrect temperature control.

SUMMARY OF THE INVENTION

It is against the above background that the present invention provides certain unobvious advantages and advancements over the prior art. In particular, the inventors have recognized a need for improvements in analyzers with exchangeable cassettes.

Although the present invention is not limited to specific advantages or functionality, it is noted that the present invention provides a filter unit integrated into at least one of the exchangeable cassettes. Thus, the air filter is no longer designed as a separate spare part but rather is integrated into an existing consumable. This ensures that the filter unit is automatically and regularly exchanged together with the consumable at certain intervals.

In accordance with one embodiment of the present invention, an analyzer, typically for analyzing body fluids, is provided which has one or more exchangeable cassettes that contain operating fluids, operating materials and/or consumables and can be inserted into corresponding holders of the analyzer. The analyzer has a system for exchanging ambient air which has a filter unit on the inlet side of the analyzer to filter the ambient air that needs to be exchanged. The filter unit is integrated into at least one of the exchangeable cassettes.

In another embodiment of the present invention, the exchangeable cassette with an integrated filter unit has a ventilation channel which is connected on the suction or pressure side to an air-conveying device, typically a ventilator, located in the analyzer and/or to air-guiding channels that are connected thereto on the analyzer side.

The filter unit can typically be integrated into a fluid pack and be exchanged together with this fluid pack.

As a result of the regular replacement of the fluid pack, for example after a predetermined period or after the operating material contained therein has been consumed, the filter unit is thus automatically exchanged with the fluid pack without requiring additional manual steps by the user. Thus, a separate training of the air filter exchange is no longer required and errors due to incorrectly carrying out the filter replacement are excluded. Furthermore, a suitably high dimensioning of the filtering efficiency and capacity can prevent an appreciable reduction of the filtering efficiency within the regular period of use of the consumable. This obviates the necessity for additional measuring devices in the analyzer for determining the degree of contamination of the air filter. In addition, separate storage and separate distribution of air filters is no longer necessary due to the integration into already existing consumables.

In yet another embodiment of the present invention, the ventilation channel in the exchangeable cassette has an outlet opening where the filter unit is located which is typically directed towards the bottom area of the analyzer. As a result when the cassette is inserted, the filter device has a horizontal, upwards-oriented approach-flow surface on which the filtrate (dust, particles, etc.) accumulates and cannot enter the analyzer when the cassette is exchanged.

In addition the ventilation channel in the exchangeable cassette can for example be U-shaped and connected on the inlet side to a suction channel which is typically arranged in the bottom area of the analyzer.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

Figure 1:
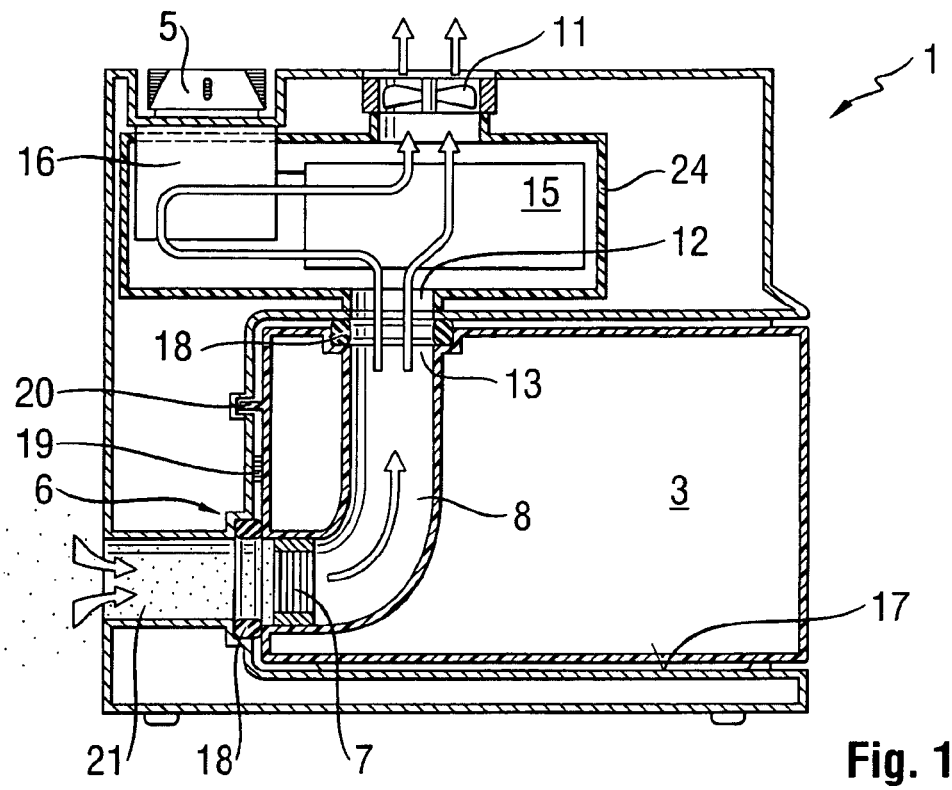
FIG. 1 shows a schematic drawing of an analyzer according to an embodiment of the invention with an exchangeable cassette.

The analyzer 1 shown in FIG. 1 is for example used for medical analyses and has an exchangeable cassette 3 which is inserted into a corresponding holder 17 of the analyzer 1. The cassette 3 is for example a fluid pack which holds the operating materials and consumables required for the operation of the analyzer. The analyzer has a system 6 for exchanging the ambient air which essentially comprises a filter unit 7 and a ventilator 11 arranged on the suction side in the analyzer as well as the required aid-guiding channels. According to the invention the filter unit 7 is integrated into the exchangeable cassette 3 and is exchanged at regular intervals with this cassette.

The exchangeable cassette 3 which holds the filter unit 7 has a ventilation channel 8 with an outlet opening 13 which is connected to corresponding inlet opening 12 of an air-guiding channel 24 in the analyzer 1 and which is sealed for example with the aid of a sealing ring 18 after the cassette 3 has been inserted into the holder 17. In the same manner the ventilation channel 8 is sealed with a sealing element 18 in the area of the filter unit 7 to the suction channel 21 of the analyzer.

After the cassette has been inserted by the user, fluidic docking nipples 19 and electrical contacts 20 automatically engage and form the required connections for the operation. The air-guiding channel 24 of the analyzer is directed at the components that need to be cooled, for example the electronic evaluation unit 15, the power supply 16 and optionally the thermostatting device etc.

Reference numeral 5 in FIG. 1 refers to an exchangeable cassette for printer paper for an internal printer.

Figure 2:
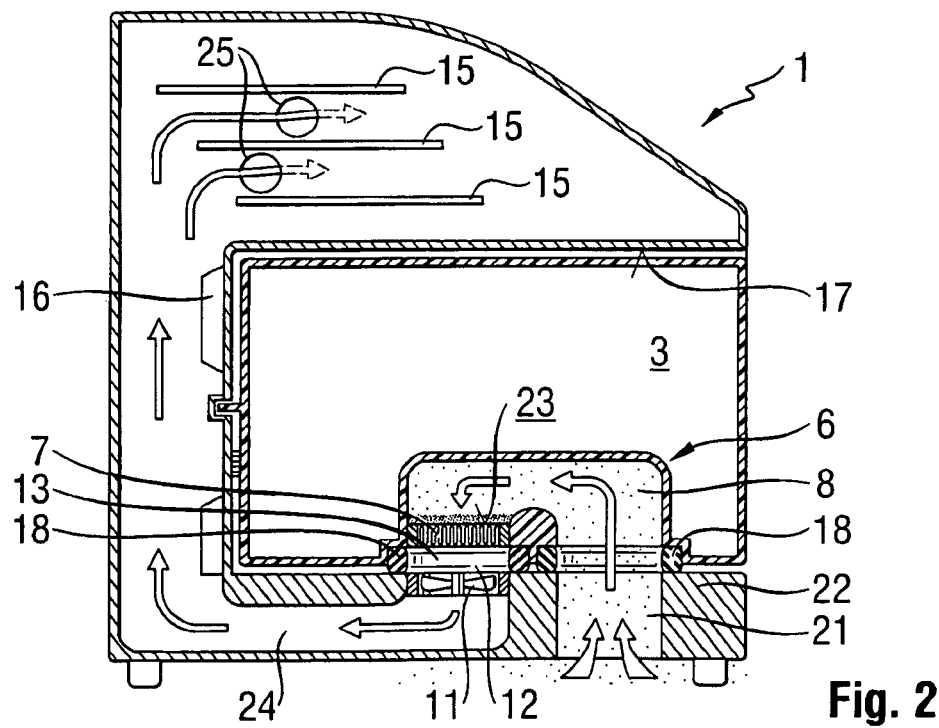
FIG. 2 shows a variant of the analyzer according to FIG. 1.

In the embodiment variant of FIG. 2 the ventilation channel 8 in the exchangeable cassette 3 has an outlet opening 13 that is directed towards the bottom area 22 of the analyzer where the filter unit 7 is located. This has a horizontally aligned approach-flow surface 23 on which the suspended particles filtered from the ambient air are deposited in the form of a dust layer indicated here by a dashed line. The dust layer remains in the filter unit 7 when the cassette is exchanged and cannot reach the analyzer.

The ventilation channel 8 is for example U-shaped in the variant according to FIG. 2 and on the inlet side is connected to a suction channel 21 in the bottom area 22 of the analyzer.

The filter unit 7 can be integrated into the fluid pack 3, for example into its base, in such a manner that the openings in the fluid pack are automatically connected to corresponding openings 12, 21 in the analyzer 1 by the correct position of the fluid pack in the analyzer in order to create a suitable air flow in the analyzer. This is achieved by appropriate guides and seals 18 on the fluid pack 3 or in the analyzer 1. The air flow can for example leave the analyzer via lateral outlet openings 25 in the area of the evaluation unit 15.

Figure 3:
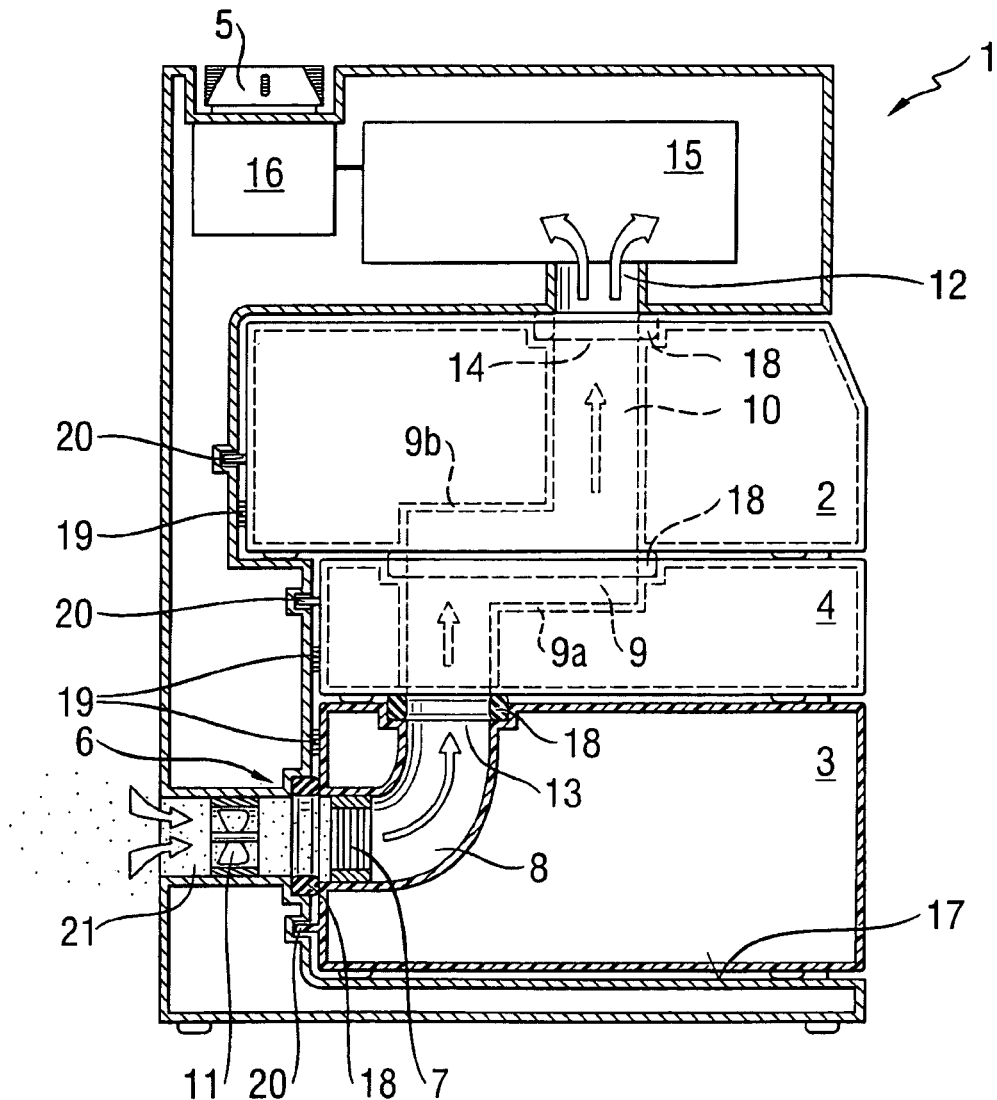
FIG. 3 shows a further embodiment variant of the analyzer according to the invention with several exchangeable cassettes.

In the embodiment variant of FIG. 3 an analyzer 1 with an exchangeable sensor cassette 2, an exchangeable fluid pack 3 and an exchangeable cassette 4 for quality control media is shown in which the filter unit 7 is also integrated in the fluid pack 3. Here the ventilation channel 8 is connected on the pressure side to an air-conveying device (ventilator 11) which is located in the suction channel 21 of the analyzer 1.

The reagent cassette 3 can also have air outlets which communicate with corresponding openings in another disposable so that these can also be supplied with filtered air. As indicated by the dashed line, parts of the air-guiding channels 9 and 10 can be formed by appropriately shaped wall sections 9a, 9b of adjacent exchangeable cassettes 2, 4 wherein the outlet opening 14 of cassette 2 communicates with the opening 12 in the analyzer.

The filter unit 7 can be composed of a fiber layer filter, a packed bed filter or a solid body filter as the filter material. The filter unit can also be composed of several individual filter layers.

The air filter does not necessarily have to be a component of the fluid pack 3 but can also be integrated into another disposable 2, 4, 5.

It is noted that terms like "preferably", "commonly", and "typically" are riot utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analyzer configured to determine body fluid parameters, said analyzer having one or more exchangeable cassettes and a temperature management system, wherein said one or more exchangeable cassettes contain operating fluids, operating materials and/or consumables and can be inserted into corresponding holders of the analyzer, wherein the temperature management system is configured to exchange ambient air and regulate temperature of analyzer internal components, which system has a filter unit on the inlet side of the analyzer to filter the ambient air, and wherein at least one of the one or more exchangeable cassettes further comprises the filter unit.

2. The analyzer according to claim 1, wherein the one or more exchangeable cassette further comprising the filter unit has a ventilation channel which on the suction or pressure side is connected to an air-conveying device located in the analyzer.

3. The analyzer according to claim 2, wherein the air-conveying device is a ventilator.

4. The analyzer according to claim 3, wherein the ventilation channel in the one or more exchangeable cassette has an outlet opening that is directed towards the bottom area of the analyzer, in which area the filter unit is arranged which has a horizontally aligned approach-flow surface.

5. The analyzer according to claim 4, wherein the ventilation channel in the one or more exchangeable cassette is configured such that on the inlet side it communicates with a suction channel.

6. The analyzer according to claim 5, wherein the ventilation channel in the one or more exchangeable cassette is U-shaped.

7. The analyzer according to claim 5, wherein the suction channel is located in the bottom area of the analyzer.

8. The analyzer according to claim 2, wherein after the one or more exchangeable cassette has been inserted into the analyzer, the ventilation channel communicates with a corresponding inlet opening of an air-guiding channel in the analyzer.

9. The analyzer according to claim 8, wherein the air-guiding channel of the analyzer is directed towards the components of the analyzer that need to be cooled.

10. The analyzer according to claim 1, wherein the one or more exchangeable cassettes include at least one exchangeable sensor cassette, at least one exchangeable fluid pack, and at least one exchangeable cassette containing quality control media.

11. The analyzer according to claim 10, wherein the filter unit is integrated into the fluid pack.

12. The analyzer according to claim 1, wherein the filter unit comprises a fiber layer filter, a granular bed filter or a solid body filter.

13. A cassette that can be exchangeably inserted into an analyzer, which analyzer is configured to determine body fluid parameters and comprises a temperature management system, the system configured to exchange ambient air and regulate temperature of analyzer internal components, which cassette contains operating fluids, operating materials and/or consumables for operating the analyzer, and wherein said cassette further comprises a filter unit for filtering said ambient air.

14. The cassette according to claim 13, wherein the filter unit comprises a fiber layer filter, a granular bed filter or a solid body filter.

15. The cassette according to claim 13, wherein the cassette is a fluid pack which contains the functional fluids required to operate the analyzer.

16. The cassette according to claim 15, wherein the functional fluids comprise calibration solutions, washing solutions, reference liquids or reagent solutions required for operation of the analyzer.

17. The cassette according to claim 13, wherein the cassette has a ventilation channel which can be connected to an air-conveying device in the analyzer on the suction or pressure side and/or to air-guiding channels that are connected thereto on the analyzer side.

18. The cassette according to claim 17, wherein the air-conveying device is a ventilator.

* * * * *